(12) United States Patent
Dushatinski et al.

(10) Patent No.: US 10,907,032 B2
(45) Date of Patent: Feb. 2, 2021

(54) GAS PHASE COATING OF BORON NITRIDE NANOTUBES WITH POLYMERS

(71) Applicant: BNNT, LLC, Newport News, VA (US)

(72) Inventors: Thomas G. Dushatinski, Chesapeake, VA (US); Diego Pedrazzoli, Newport News, VA (US); R. Roy Whitney, Newport News, VA (US)

(73) Assignee: BNNT, LLC, Newport News, VA (US)

( * ) Notice: Subject to any disclaimer, the term of this patent is extended or adjusted under 35 U.S.C. 154(b) by 0 days.

(21) Appl. No.: 16/319,207

(22) PCT Filed: Jul. 20, 2017

(86) PCT No.: PCT/US2017/043140
§ 371 (c)(1),
(2) Date: Jan. 18, 2019

(87) PCT Pub. No.: WO2018/017870
PCT Pub. Date: Jan. 25, 2018

(65) Prior Publication Data
US 2019/0276635 A1 Sep. 12, 2019

Related U.S. Application Data

(60) Provisional application No. 62/364,490, filed on Jul. 20, 2016, provisional application No. 62/427,506, filed on Nov. 29, 2016.

(51) Int. Cl.
*C08K 9/04* (2006.01)
*A61K 9/00* (2006.01)
(Continued)

(52) U.S. Cl.
CPC ............ *C08K 9/04* (2013.01); *A61K 9/0092* (2013.01); *C01B 21/0648* (2013.01);
(Continued)

(58) Field of Classification Search
CPC ....................................................... C08K 9/04
See application file for complete search history.

(56) References Cited

U.S. PATENT DOCUMENTS

2006/0098389 A1  5/2006  Liu et al.
2010/0051879 A1  3/2010  Sainsbury et al.
(Continued)

FOREIGN PATENT DOCUMENTS

EP     3 249 472     11/2017

OTHER PUBLICATIONS

International Search Report for PCT/US2017/043140 dated Oct. 13, 2017, 2 pages.
(Continued)

*Primary Examiner* — Larry W Thrower
(74) *Attorney, Agent, or Firm* — Joshua B. Brady; Nixon & Vanderhye, P.C.

(57) ABSTRACT

Boron nitride nanotube (BNNT)-polyimide (PI) and polyxylene (PX) nano-composites, in the form of thin films, powder, and mats may be useful as layers in electronic circuits, windows, membranes, and coatings. The processes described chemical vapor deposition (CVD) processes for coating the BNNTs with polymeric material, specifically PI and PX. The processes rely on surface adsorption of polymeric material onto BNNTs as to modify their surface properties or create a uniform dispersion of polymer around nanotubes. The resulting functionalized BNNTs have numerous valuable applications.

23 Claims, 3 Drawing Sheets

(51) Int. Cl.
    *C01B 21/064* (2006.01)
    *C08G 61/02* (2006.01)
    *C08G 73/10* (2006.01)
    *C08K 3/38* (2006.01)
    *D01F 9/08* (2006.01)
    *C08K 3/28* (2006.01)
    *C08L 33/24* (2006.01)
    *C08K 9/08* (2006.01)

(52) U.S. Cl.
    CPC ....... *C08G 61/025* (2013.01); *C08G 73/1028* (2013.01); *C08K 3/28* (2013.01); *C08K 3/38* (2013.01); *C08K 9/08* (2013.01); *C08L 33/24* (2013.01); *D01F 9/08* (2013.01); *C01P 2004/13* (2013.01); *C08G 2261/11* (2013.01); *C08G 2261/312* (2013.01); *C08G 2261/964* (2013.01); *C08K 2003/385* (2013.01); *C08K 2201/011* (2013.01)

(56) References Cited

U.S. PATENT DOCUMENTS

2011/0192016 A1    8/2011    Kang et al.
2013/0119316 A1    5/2013    Sauti et al.

OTHER PUBLICATIONS

Written Opinion of the ISA for PCT/US2017/043140 dated Oct. 13, 2017, 7 pages.

Yanagishita H. et al., "Preparation of polyimide composite membrane by chemical-vapor-deposition and polymerization technique (CVDP)", Journal of Applied Polymer Science, 1993, vol. 49, issue 4, pp. 565-572; retrieved from the Internet: <DOI: 10.1002/app.1993.070490402>.

Hutchins C. W. et al., "Apparatus for chemical vapor deposition of polymide films", Review of Scientific Instruments, 1995, vol. 66, issue 7, pp. 3943-3947; retrieved from the Internet: <DOI: 10.1063/1.1145399>.

Putkonen M. et al., "Atomic layer deposition of polyimide thin films", Journal of Materials Chemistry, 2006, vol. 17, issue 7, pp. 664-669; retrieved from the Internet: <DOI: 10.1039/B612823H>.

Demirel M.C. et al., "Spatially Organized Free-Standing Poly(p-xylylene) Nanowires Fabricated by Vapor Deposition", Langmuir, 2007, vol. 23, issue 11, pp. 5861-5863; retrieved from the Internet: <DOI: 10.1021/la700538f>.

Goldberg D. et al., "Boron Nitride Nanotubes and Nanosheets", ACS Nano, 2010, vol. 4, issue 6, pp. 2979-2993; retrieved from the Internet: <DOI: 10.1021/nn1006495>.

Extended European Search Report for EP 17 83 1894 dated Mar. 16, 2020.

C.Y. Zhi et al., "Boron Nitride Nanotubes: Functionalization and Composites", Journal of Materials Chemistry, 2008, vol. 18, pp. 3900-3908.

Zhi, C. et al., "Boron Nitride Nanotubes", Materials Science and Engineering: R: Reports, Elsevier, Amsterdam, NL, vol. 70, No. 3-6, Nov. 2010, pp. 92-111.

GAS PHASE COATING OF BORON NITRIDE NANOTUBES WITH POLYMERS

This application is the U.S. national phase of International Application No. PCT/US2017/043140 filed Jul. 20, 2017 which designated the U.S. and claims priority to U.S. Provisional Application Nos. 62/364,490, filed Jul. 20, 2016, and 62/427,506 filed Nov. 29, 2016, the entire contents of each of which are hereby incorporated by reference.

STATEMENT REGARDING GOVERNMENT SUPPORT

None.

FIELD

The present disclosure relates to forming functionalized BNNTs, and in particular, vapor deposited polymer materials and inorganic nanotubes, and in particular, boron nitride nanotube and polyimide, poly-p-xylxylene,

BACKGROUND

Polymer materials incorporating boron nitride nanotubes (BNNTs) are desirable for their improved properties, including as examples, high strength, good electrical insulation, potentially low dielectric constant, and good thermal conductivity. However, they typically have relatively low BNNT content and when in polymer/BNNT composite films, the film thickness is typically greater than 50 μm. Low BNNT content and such relatively thick films limit the usefulness of the composite material, and consequently they have limited applications. Generally, the terms "thin film" and "thin wafer" refer to composites having a film thickness of about 50 μm or less, and are dense and/or compacted. Mesh films, on the other hand, are generally porous when deposited. Typical polyimide films are produced through codeposition of polyamic acid (PAA) that is composited with BNNT. The resulting material loses structural integrity at loadings above about 40 w % because of inhomogeneity of polymer distribution. Thus, improved film uniformity and homogeneity, as well as enhanced control over film thickness, are desired.

As described herein, gas phase deposition of PAA precursors allows for surface adsorption of gases and polycondensation of chains homogenously. Commercial processes involve solvation of diamine and dianhydride monomers in polar aprotic solvents to form the intermediate product, PAA, in a condensation reaction, followed by deposition and an imidization process to create composites. Significant challenges in forming BNNT-polyimide composites in solution result from the high quality BNNTs making the precursor materials too viscous, due to the long fibril characteristics of the nanotubes and inhomogeneity of composite films caused by agglomeration of like constituents.

Parylene (poly-p-xylxylene) conformal coatings have been utilized in the electronics industry as moisture barrier protection. It would therefore be desirable to coat BNNT surfaces with parylene. Surface coating BNNTs with parylene has applications in structural and thermal composites as well as highly porous membranes. The process typically involves vaporization of di-p-xylene around 175° C. whereby it is fed through a pyrolysis furnace (600-700° C.) and evolved into p-xylene monomer and fed into a deposition chamber. Poly-p-xylene condenses on surfaces as the monomers react resulting in a conformal coating. The ability to create quality coatings onto tube surfaces creates unique nanocomposites that are functional as membranes when coatings are preformed on buckypapers. Furthermore, poly-p-xylene coated nanotubes have different solubility properties and interfacial faces with polymer matrices.

SUMMARY

This disclosure describes methods of forming boron nitride nanotube (BNNT)-polyamic acid (PAA), polyimide (PI) and poly-p-xylene (PX) composites and other thermoplastic and thermosetting composites, and in particular, processes to form BNNT-PX, PI, and PAA nano-composites with high compositions of BNNTs. The methods described herein may produce thin films ranging from about 100 nm to about 100 μm (and above, if desired), and are particularly suited for forming thin film coatings on BNNT surfaces. The resulting functionalized BNNTs have a wide range of valuable applications. These films are useful for, as examples only, layers in electronic circuits and x-ray windows, among other valuable uses. Generally, the present approach involves the chemical vapor deposition (CVD) of polymeric material on nanotubes, and in particular BNNTs. It should be appreciated by those of ordinary skill in the art that variations in the disclosed embodiments are contemplated and may be made without departing from the present approach. CVD processes may be used for coating the BNNT material, which may be, as examples, one or more of a BNNT puff ball, BNNT powder, BNNT buckypaper, BNNT woven fiber mat, BNNT fibers, BNNT porous scaffolding, or BNNT densified wafers, with the monomers. Some embodiments may employ one or more heating steps to drive polymerization and imidization, resulting in the PI coatings on the BNNTs. The thermal transition temperature of the pro PAA monomers to PAA in gas phase methods is 170° C. or at around this temperature. Further thermochemical transitions occur at approximately 270° C. in the cyclization of PAA chains in the imidization reaction. Crystallinity and chain length may be tuned through gradient heating between 1 and 100° C./min with thermal plateaus to optimize reactions. Other thermosetting polymers have similar behavior.

Likewise, PX may be deposited in a system that has a chamber for vaporization of PX precursor. The precursor may be pyrolyzed into monomer and the temperature and pressure adjusted to allow the monomer to condense as PX onto BNNT surfaces. The process may involve vaporization of di-p-xylene at around 175° C. and then feeding the material through a pyrolysis furnace (at about 600 to about 700° C.). The material may then be evolved into p-xylene monomer and fed into a deposition chamber. Poly-p-xylene condenses on surfaces as the monomers react resulting in a conformal coating. The surfaces may include BNNT materials within in the chamber. The BNNT material may be, for example, one or more of a BNNT puff ball, BNNT powder, BNNT buckypaper, BNNT woven fiber mat, BNNT fibers, BNNT porous scaffolding, or BNNT densified wafers. In some embodiments, the BNNT material may be supported by a temperature-regulated structure, such as a scaffolding.

By utilizing high quality BNNTs, i.e., BNNTs having few walls, few defects, length to diameters typically over 10,000 (high aspect ratio), diameters less than 10 nm, highly crystalline and catalyst free, BNNT-PI and BNNT-PX can be created that are useful as electrically insulating, thermally conductive layers in electronic circuits and as thin windows for x-ray, vacuum ultraviolet, porous membranes, etc. equipment.

It should be appreciated that BNNTs functionalized according to an embodiment of the present approach have numerous advantageous uses. BNNTs surface coated in PI, PAA, and PX can be suspended in a non-solvent, composited into a thermoplastics and thermosets, composited into an epoxy, polyurethane, polystyrene, polyisoprene matrix and formed into parts, sheets, coatings, and adhesives. The present approach further allows for drastically more uniform and homogenous thin film coatings.

Embodiments of a process for synthesizing functionalized BNNTs are disclosed. Generally, a BNNT material is positioned on a support in a chamber. The support may be temperature regulated, such that the support temperature may be controlled independent of the chamber temperature. The chamber may be heated to evaporate monomers in the chamber, allowing for a gas phase deposition of monomers onto the BNNT material. The support may be cooled to drive condensation of monomers on the BNNT material, to form a functionalized BNNT material. The cooling may be selectively set to condense a specific monomer, while other monomers remain in the gas phase. The BNNT material may initially take the form of at least one of a BNNT puff ball, a BNNT powder, a BNNT buckypaper, a BNNT woven fiber mat, or a BNNT porous scaffolding.

In some embodiments, the deposition chamber may be a Knudsen cell configured to control the evaporation of the first monomer and the second monomer through temperature and pressure regulation within the chamber. In some embodiments, the deposition chamber may be connected to a vaporization and pyrolyzing chamber to produce p-xylene monomer from di-p-xylene.

Some embodiments may feature two or more monomers. The monomers may be monomers of polyimide. In some embodiments, a first monomer may be an anhydride, and a second monomer may be a diamine. The first and second monomers comprise monomers of poly(p-xylene). As another example, the first monomer and the second monomer may be selected to form a polyamic acid film on the BNNT material. As yet another example, the first monomer may be diamine, and the second monomer may be an anhydride gas. The first and second monomers may be introduced into the chamber simultaneously, or alternatively introduced alternatingly into the chamber. As an example, the first and second monomers are introduced alternatingly into the chamber, and an alternating cycle between the first and second monomers is less than about 100 Hertz. If desired, monomers may be introduced initially at the same time, and later monomers may be introduced in an alternating fashion. The inverse is likewise contemplated. Depending on the desired outcome, the process may continue for about one hour. In some embodiments, the functionalized BNNT material may be imidized to form a polyimide coated BNNT nano-composited material.

It should be appreciated that the selected monomers may be feed into the chamber at a desired rate. For example, the feed rate of p-xylene may be controlled by the vaporization rate of di-p-xylene. With respect to the functionalized BNNT material, poly-p-xylene coated BNNTs may function as surface modified nanotubes. Also, polyamic acid and polyimide coated BNNTs may function as surface modified nanotubes. The functionalized BNNT material may be processed into a desired form factor. For example, the functionalized BNNT material may be compressed to form a non-woven mat. As another example, functionalized BNNT material may be suspended in a non-solvent. The non-solvent solution may have at least one of a metal, a ceramic, and a polymer matrix material. Additional processing may include, but is not limited to, vacuum filtering the functionalized BNNT material and casting the functionalized BNNT material to form a porous non-woven mats.

Depending on the desired end application, one or more nanoparticles may be absorbed within the functionalized BNNT material. The nanoparticle may include one or more of a medicine, a metal, a ceramic, and a semiconducting material. The nanoparticle can be activated by electromagnetic radiation, including photons, or by nuclear radiation.

DETAILED DESCRIPTION

Figure 1:
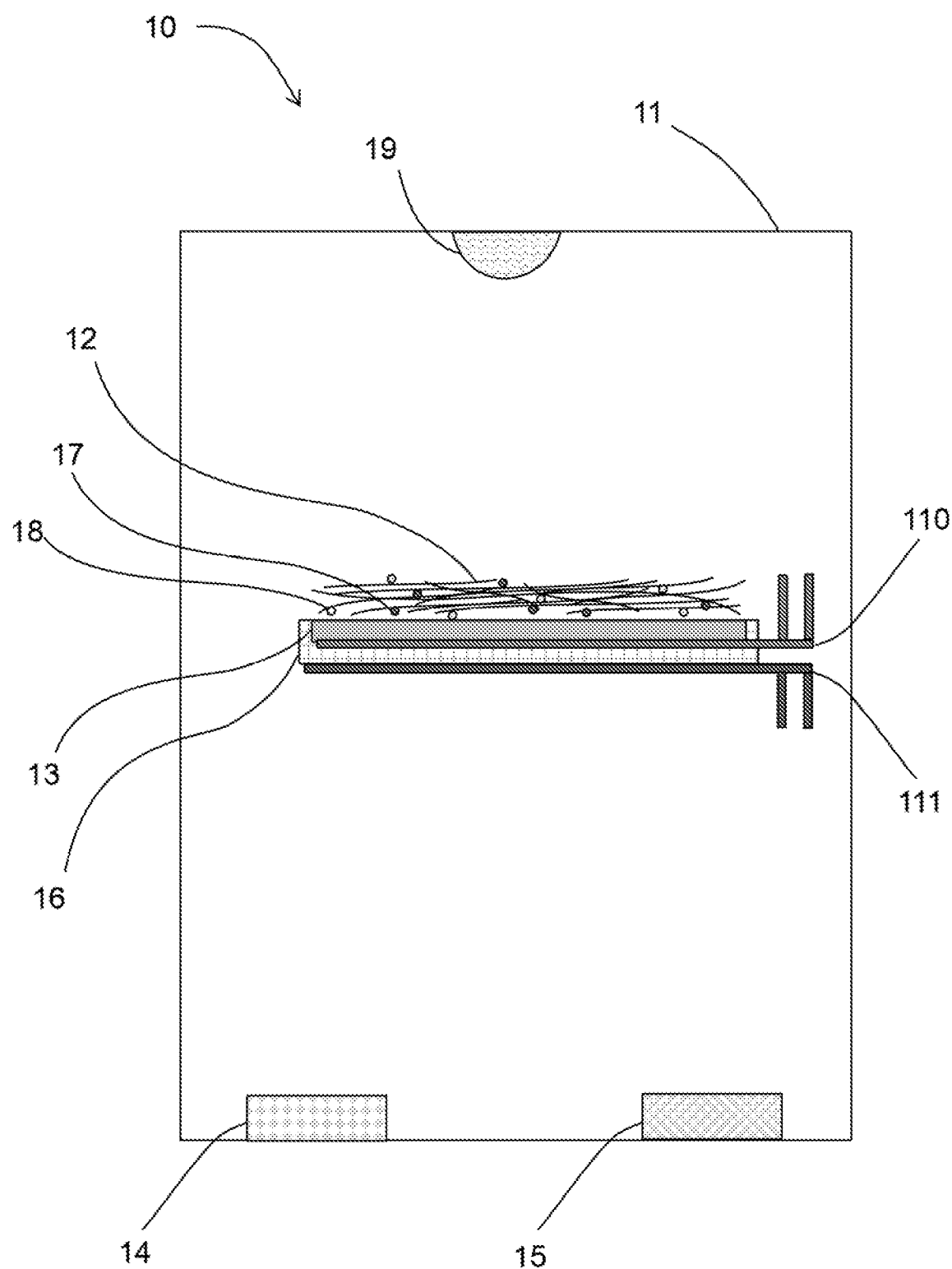
FIG. 1 illustrates a reaction chamber for deposition of PAA and poly-p-xylene into a BNNT mat, according to an embodiment of the present approach.

BNNTs functionalized under the present approach have numerous valuable applications. For example, applications that require electrical insulation and thermal conductivity will benefit from highly crystalline, thermally stable composites of boron nitride nanotubes (BNNT) and polyimide (PI) and poly-p-xylene (PX). Examples include electronic circuits having single diodes to billion-element electronic integrated circuits, membranes, and low-energy x-rays windows. Other applications include silicon wafer bonding material, substrates for printed circuit boards, and heat sync coatings for circuit boards and electrical components. These are merely examples of the numerous potential applications for BNNT surface coated through gas phase processes to form nano-composite materials. The term "nano-composite" generally refers to a nanotube that is surface coated with a polymer, altering its diameter because of the surface adsorption of polymers. Properties of standalone nano-composites of BNNT and PI are prized for their enhanced characteristics of thermal conductivity due to the stabilizing effect of the BNNT. Likewise, PX is surface stabilized and less chemically active when coated onto a BNNT. PX and BNNT nanocomposites are an alternative to polyethylene membranes. Embodiments of such functionalized BNNTs, and of processes for synthesizing them, are described below. It should be appreciated that departure from the specifically disclosed embodiments may be made without departing from the present approach.

The BNNTs may go through a purification step prior being placed on a surface for polymer treatments (for any of methods described herein). Purification of BNNTs may include acid treatment to remove boron, amorphous boron nitride and hexagonal boron nitride particulates with controlled pH or spectroscopic in situ analytics. While these impurities also have high dielectric performance, their thermal properties are not beneficial for dissipative applications. Therefore, purification of the initial BNNT material may involve the following methods. Acids, such as nitric acid or other oxoacid and superacid variants, may be used. Additionally, the acid(s) may be at an elevated temperature such as, for example, 30° C. to 200° C., to increase the reaction rate on active regions, specifically crystal edges of BNNTs and impurities. The acid treatment may be followed by ample rinsing with, for example, deionized water, to neutralize the product and prevent further oxidative reactions and to remove the oxidized constituents. BNNT purification may involve further steps, such as those described in U.S. Provisional Application No. 62/427,506, which is incorporated by reference in its entirety. For example, purification may involve an oxygen feedstock to evolve unwanted boron and boron nitride to oxygen saturated borates. Simultaneously a hydrogen feedstock evolves the borates to hydrogen borates that sublime at the elevated process temperature.

Contemporary methods produce films on BNNTs with insufficient thermal conductivity, because of the low BNNT composition. The present approach provides methods for synthesizing BNNT-based PI and PX composite materials. As described herein, these multi-step processes may be used to synthesize BNNT-PI and BNNT-PX composites, and overcome the limitations of low density of BNNT in polymer matrices. The resulting functionalized BNNTs have numerous advantageous uses.

Generally, embodiments of the present approach involve an initial BNNT material. The BNNT material comprises at least one of a BNNT puff ball, a BNNT powder, a BNNT buckypaper, a BNNT woven fiber mat, or a BNNT porous scaffolding. The BNNT material may be prepared by, for example, by deposition of a thin film onto a substrate capable of resisting surface interactions with the walls of the BNNTs, freeze drying purified boron nitride nanotubes into powder form or porous scaffolding, pelleting boron nitride nanotubes through compression, or evaporative deposition or vacuum filtration of a BNNT suspension into a buckypaper. These BNNT form factors maintain porosities appropriate for permeation of monomer gases throughout the BNNT material, and allow for homogenous surface coating of the nanotubes. Other BNNT materials may be suitable, provided that they include adequate porosity. Processes for forming the BNNT form factor typically leave impurities such as organic residues on the surface of BNNTs. Thermal treatment may be used to remove residual solvents on BNNT surfaces. Time intervals and temperature(s) for thermal treatment may vary depending on the embodiment, but generally depend on the type solvent and its heat of vaporization. Due to substrate interactions with the walls of the BNNTs, substrates for thin films of BNNT may be selected for optimization of adhesion or exfoliation properties depending on the application and successive method fabrication techniques. Suggested substrates for deposition/filtration and successful exfoliation include, for example, undoped silicate, aluminum, silicon, and n-doped silicon and aluminum oxide wafers and filters. If the BNNT-PI and BNNT PX composite material is to be removed from the substrate, p-doped functioning and polymeric materials may not be the most suitable for exfoliation. If the final BNNT-PI and BNNT-PX film is to remain on the substrate, the substrate material may be selected to optimize adhesion of the film to the substrate; for example, boron doped silicon will have higher adhesion than phosphorous doped silicon. In some embodiments, the substrates may have root mean square (RMS) roughness under 100 nm for roll-to-roll exfoliation and other techniques that require low friction and mechanical hindrances. A scanning tunneling (STM), atomic force microscopy (AFM), and surface profilometer equipment are generally used to measure surface topography. An RMS roughness is the average variance of surface height across a scanned two-dimensional section where the measured variable is the z-axis corresponding to surface height. Selection of substrates for calendaring of the BNNT-PI and BNNT-PX should have melting temperatures above 250° C.

BNNT material may be processed further prior to coating, which may be useful for certain form factors. For example, following powderization through freeze drying or deposition as buckypaper and removal of the solvent, the resultant BNNT mat may be calendared to reduce its thickness. Some BNNT synthesis processes produce a BNNT puffball form factor, which may also be used. The calendaring surface may be n-doped silicon or similar material so that it is removable following the calendaring step in the process. The process of calendaring involves the compression of a deposited film to increase density and decrease porosity. It is preferred to fabricate nanocomposites of polymer on BNNT on clean and purified nanotubes with higher surface area form factors such as the original puff ball because of the fibrilization that occurs when the material is allow to agglomerate. Varying levels of compression can be achieved with hydraulic and mechanical presses. The band gap of BNNTs is around 5.7 eV. Improved dielectric properties can be achieved through improvements to porosity, such as in as deposited films that contain a larger amount of void regions that are electrically isolating. However, more dense films of BNNTs will have higher thermal conductivity. The calendaring process may also result in some in-plane alignment of the BNNTs in the plane of the substrate.

BNNTs in varying form factors may be composited with pro-PAA monomer, PAA, pro-poly-xylene monomer, or poly-xylene. Embodiments described herein involve surface adsorption of the monomer to a BNNT material, which may then undergo further thermochemical processes to synthesize BNNT-composites. In some embodiments, the methods may be used to synthesize sulfonated variants of BNNT-PI or ortho, meta BNNT-poly-x-parylene composite materials. In some embodiments deposition is over a porous thin film of BNNTs followed by calendaring. In other embodiments monomer deposition may be performed over a precalendared BNNT thin film.

After BNNT material deposition, the BNNT material may undergo surface treatment with pro variant PAA or pro variant PX monomers in gas phase. Monomer deposition in the gas phase dramatically improves uniformity and homogeneity of the film, and when regulated also allows for deposition of thin and ultra-thin films. These processes may be performed in, for example, a Knudsen cell, or alternatively in a cell that allows gas material to fill a chamber and condense onto BNNTs loaded onto a substrate. Spassova describes a process for utilizing CVD to synthesize PAA and furthermore PI. See Spassova, E. "Vacuum deposited polyimide thin films", Vacuum. 70, pp. 551-61, (2003). However, Spassova merely performs a CVD process for coating items such as a sheet of silica with PI. Spassova's process does not provide nanoscale conformal coatings, and would be inadequate for forming functionalized BNNTs as taught by the present approach.

Under the present approach, the process permits uniform deposition of dissimilar monomers on nanotubes, including form factors of BNNT puff ball, a BNNT powder, a BNNT buckypaper, a BNNT woven fiber mat, or a BNNT porous scaffolding. FIG. 1 illustrates an embodiment of a modified Knudsen cell 11 containing a BNNT mat 12 applied to a substrate 13. Holder 16 supports BNNT mat 12 and substrate 13 within the cell 11. Typically, cell 11 is evacuated at start-up and maintained at partial pressure during the process. During CVD processing, PAA and PX monomer constituents, to be discussed in FIGS. 2 and 3, such as ODA 14, PMDA 15, are heated to evaporate the monomers into the Knudsen cell 11 or pyrolyzing furnace (not shown). Monomers may be co-evaporated, or may be alternatingly evaporated at a desired rate. For example, some embodiments may involve an alternating cycle between the first and second monomers that is less than about 100 Hertz. It should be appreciated that the monomers may be varied without departing from the present approach. The temperature of the Knudsen cell 11 should be sufficiently high to preclude monomer condensation or collection on the walls of the Knudsen cell 11. The substrate 13 may be held at a sufficiently low temperature to drive polycondensation of monomers 17 and 18, collection on the substrate 13 and on the BNNT mat 12. The support or holder 16 may be heated to maintain a temperature similar to the Knudsen cell 11 temperature, while the upper surface of the holder 16 may be slightly cooled to drive the monomers 17 and 18 condensation/collection on the substrate 13 and the BNNT mat 12. Heating and cooling loops 110 and 111 may be used to heat and cool the holder 16 and the substrate 13 such that the monomers 17 and 18 collect only on substrate 13 and BNNT mat 12 surfaces. Alternate embodiments may use thermal electric elements to provide heating and cooling to the holder 16 and substrate 13. An infrared radiant element 19 may be present to create a temperature gradient across the BNNT mat 12. A temperature gradient may control the preferential collection of monomers 17 and 18, so that, for example, monomers 17 and 18 preferentially collect from the substrate 13 side of the BNNT mat 12, through the BNNT mat 12, and then finally on the external (e.g., top) side of the BNNT mat 12. In some embodiments, the substrate 13, BNNT mat 12, holder 16, and infrared heater (if present) may be inverted, such that the CVD process proceeds downwards rather than upwards, would occur in the configuration shown in FIG. 1. In some embodiments the substrate 13, BNNT mat 12, holder 16 and associated support (not shown), heating and cooling components may be rotated or oscillated such as to assist in making the CVD process uniform across the entire surface area of the BNNT mat 12. It should be appreciated that the BNNT material (e.g., the form factor), may be different than the mat 12 shown in FIG. 1, without departing from the present approach.

In some embodiments, the amounts of ODA 14 and PMDA 15 monomers used in the process are of generally equal molar value or with minimally excess dianhydride: diamine (e.g., 52:48 w:w), and controlled to supply the desired level of CVD to the BNNT mat. In some embodiments, including an additional thin layer or layers of monomers, may also include additional material for forming a thin layer of monomers 17 and 18. In some embodiments, the additional thin layers of monomers 17 and 18 (which may be the same monomers or may be new monomers, for example) deposit across the outer layer of the BNNT mat 12. The additional material for the outer layer may be desirable so as to create a smooth, chemically homogenous final surface. Relative monomer amounts may be adjusted to generate the desired end product. In some embodiments, the additional layers may of different chemistry to include molecules that may be of medical use, metalloids for creating metal groups or quantum dots on the surface, molecules or atoms that may have catalytic properties, and molecules or atoms that may be excited by electromagnetic radiation, to include photons, or nuclear radiation. In some embodiments, the monomers both for the initial layers and the possible additional layers by be introduced cyclically where the relative vapor pressures of the monomers are varied in time, the temperature of the walls of the cell are varied in time, and the temperature and temperature profile of the scaffold holding the BNNT mat is varied in time. As one skilled in the art of CVD is aware, the times, temperatures and pressures of all of the components of the system all affect the CVD process.

Following the CVD process for collecting the PAA monomers 14 and 15 on the BNNTs in the BNNT mat 12, and the outer coating (if present), calendaring may be used to decrease film thickness of the BNNT mat 12 with the collected monomers 17 and 18. Calendaring of BNNT mats before monomer treatment and before PAA conversion of pro PAA monomers at 100° C. to 250° C. are considered. Next, thermal treatment may be used to form PAA intermediate and final PI throughout the BNNT mat 12 via the polymerization and imidization processes. The important thermal transitions (thermochemical reactions) of pro PAA monomers are 100° C. to 200° C. (polycondensation of dianhydride and diamine monomers) and between 220° C. and 300° C. for imidization of PAA. For example, in some embodiments, thermal treatment may be carried out in intervals between 100 and 300° C. on the order of 1-100° C./min over the intervals and holding at the desired temperature for optimization that includes improvement to PI molecular weight and crystal grain size. In some embodiments, the final BNNT-PI films may be exfoliated, though roll to roll processing, contact resist exfoliation, and embodiments that involve removal by rinsing the film off of the deposition surfaces in all methods.

PX coatings on BNNTs may be synthesized in a similar manner. Clearly, the starting monomer is different. PX is typically deposited from a dimer feedstock, for example ortho, meta, or para xylene, the arene substitutions. Di-para-xylene is the most common feedstock for preparation of xylene monomer feedstock. PX monomers are prepared via vaporization of dimer at 40 to 200° C. into a pyrolyzying furnace that is between 400 to 700° C. After pyrolyzing, the monomer exists as the monomer of the dimer used. The monomer condenses onto surfaces within the deposition chamber with the same arene functionalization as the feedstock.

For BNNT-PI, BNNT-PAA, and BNNT-PX films that are to be removed from the substrate a resist may be utilized. Resists are defined as materials desired for thin film processing that are easily removed to obtain desired films or other form factors. Resists in some embodiments may be solvated for easy removed through rinsing. These processes depict polymer or metallic films that may be etched through solvent or acid solvation. For example, an aluminum film may be used in the calendaring process and subsequently removed by, for example, phosphoric acid, then rinsed away leaving behind a calendared BNNT wafer. In some embodiments, monomer heat treatment, treatment converting monomers to PAA, can be performed after isolation and drying of the BNNT film onto a filtration membrane. The substrate used for monomer treatment and support for acid treatment may vary depending on the embodiment, and may depend on whether the membrane is to be part of the final BNNT-IP film, or instead the membrane is to be removed from the BNNT-PI film. In some embodiments, filtration membranes that remain in the BNNT-PI film may be formed from materials with melt temperatures above 200° C., and have significant acid stability. Otherwise, the filtration membrane may contaminate the resulting BNNT-PI film. This process may significantly decrease polyimide composition as compared to embodiments of described above. However, for purposes of binding BNNTs for successful exfoliation of films from the substrate, calendaring after monomer treatment may be used in some embodiments.

Figure 2:
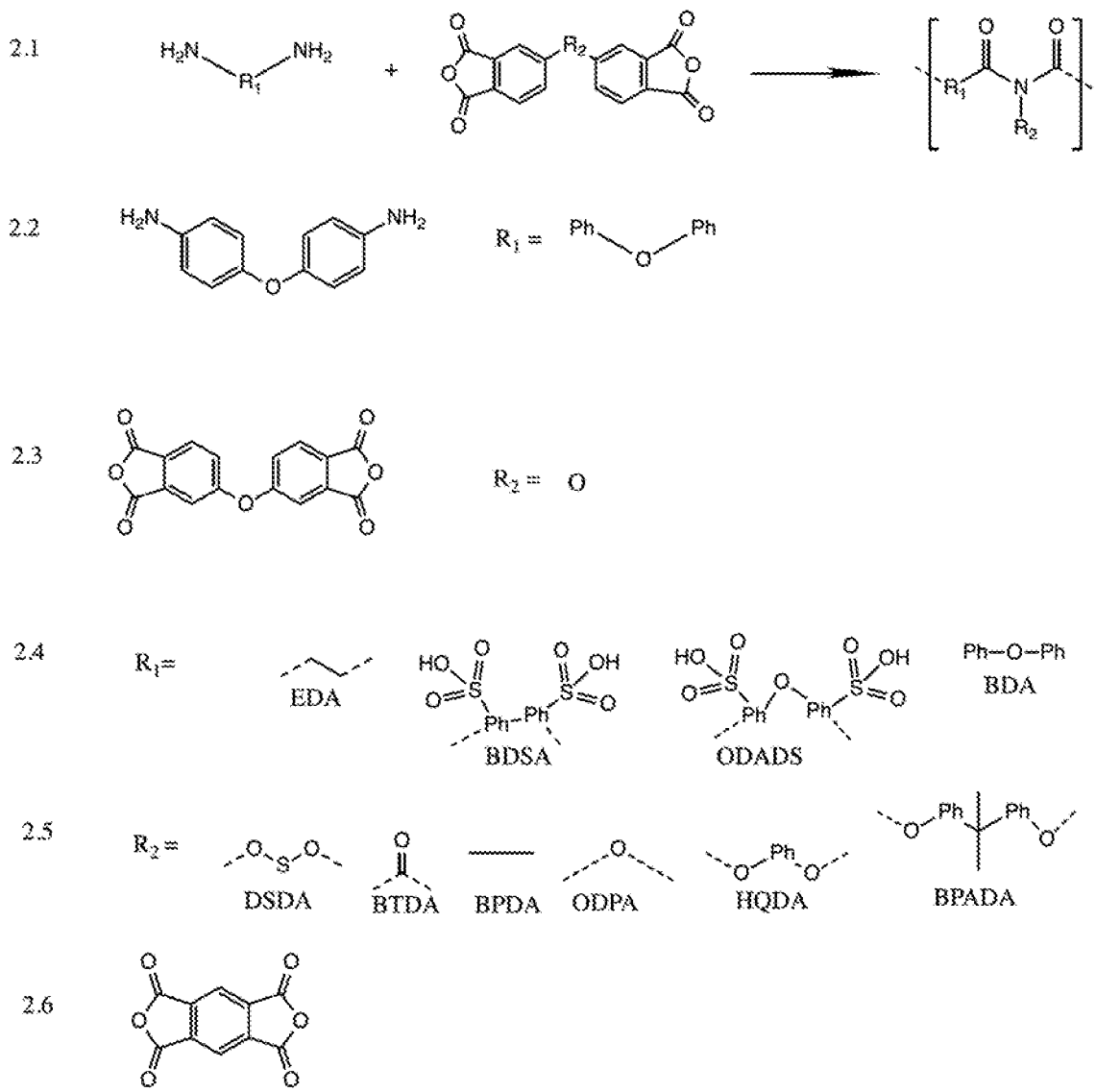
FIG. 2 shows the general reaction of a diamine with a dianhydride to produce a polyimide and base chemical structure of dianhydrides and diamines with some common functionalities used to make functionalized BNNT-PAA and BNNT-PI materials.
Figure 3:
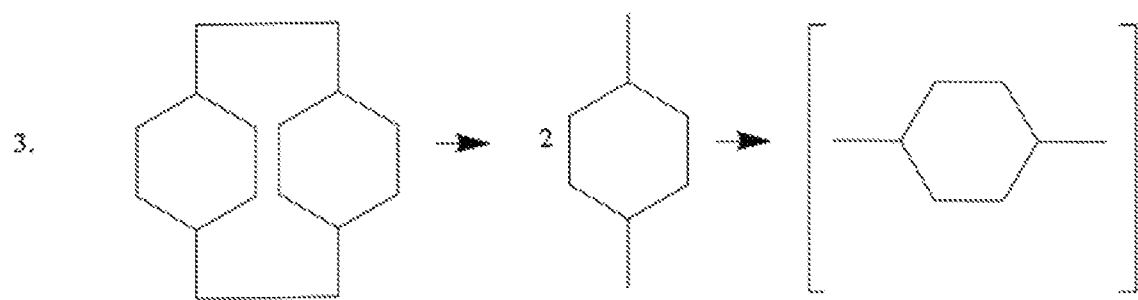
FIG. 3 shows the general reaction of di-para-xylene that degrades to para-xylene then condenses as poly-para-xylene in a deposition chamber.

FIG. 2 shows the chemical processes for preparation of PAA and PI. The reaction of diamine and dianhydride progress as shown in FIG. 2.1. Embodiments of the methods described herein may include variants of diamine and dianhydride monomers on the basis of varied R-groups, such as the examples shown in FIGS. 2.2, 2.4 and 2.3, 2.5 respectively. Other embodiments may utilize other R-groups. FIG. 2.1 shows the monomers of PI and PI final chemical structure dehydration polymerization reaction. FIG. 3 shows the chemical processes for preparation of PX.

The techniques involving solutions of monomers into solvents and gas phase depositions of pro PAA and PX monomers may require pretreatment of monomers to reduce water concentrations in the reaction cell. Water undesirably terminates propagation of PAA chains. Dehydration of the monomers may be performed prior to dispersion or monomer treatments to reduce detrimental termination.

In general, gas phase CVD produces longer chains of PX, PAA intermediate and PI final product, compared with wet chemistry processes. Gas phase deposition is preferable over liquid phase depositions of PAA or pro PAA monomers because anhydrous environments are preferred to synthesize high density and crystallinity in PI chains. Thermal treatment reduces the energy of the final product, through increases in crystallinity that are optimally chemically stable, and results in a highly crystalline BNNT-PI composite film. It should be appreciated that higher crystallinity in the BNNT-PI composite material results in high thermal conductivity, and thus enhancing crystallinity leads to optimal thermal conductivity through improvements to grain sizes and phononic channels that increases phonon mobility. Additionally, the BNNT sidewalls function as crystal templates for aiding propagation of the PAA resulting in higher PAA chain lengths along the BNNT's surfaces.

Other polymers may deposited and composited with the BNNTs via CVD in a manor similar to the monomers going into the PI. The temperature level and temperature gradient described herein, where a temperature difference is created across the BNNT layer by cooling on one side of the mat and heating on the other side of the mat, can be used to control the rate of deposition across the BNNT layer and for a final surface coating of the polymers. Calendaring under vacuum or reduced pressure may also be utilized to reduce voids.

Alignment of BNNTs in the substrate plane and out of plane is important for enhancements to thermal conductivity. Depending on the desired thermal dissipation parameters, tube orientation will be manipulated to sufficiently act as phononic pathways. Orientation of BNNT mats is typically randomly orientated and may suffice for out of plane thermal conductivity and calendared BNNTs orient in plane for in plane thermal conductivity. Additionally, BNNTs are chemically inert support materials that may also function as a capsule. The hollow cavity within a BNNT can absorb nanoparticles, such as, for example, medicines, metals, ceramics, and semiconducting nanoparticles, and protect such nanoparticles from chemical degradation. BNNTs absorb solvent readily, therefore when nanoparticles are dispersed into solvents they are absorbed into nanotubes. Encapsulating the entirety of a BNNT with PX or PI allows for a packaging of species that may degrade and be constituted of biocompatible polymer or may be further functionalized to be biocompatible.

The methods described in the present approach may be embodied in other specific forms without departing from the spirit or essential characteristics thereof. The disclosed embodiments are therefore to be considered in all respects as illustrative and not restrictive by the foregoing description.

We claim:

1. A process for synthesizing functionalized boron nitride nanotubes (BNNTs), the method comprising:
    positioning a solid BNNT material on a support in a chamber, the solid BNNT material comprising a plurality of BNNTs having surfaces;
    heating the chamber to evaporate a first monomer and a second monomer in the chamber;
    cooling the support to drive condensation of the first monomer and the second monomer onto surfaces of the BNNTs in the solid BNNT material to form a solid functionalized BNNT material comprising surface-coated BNNTs.

2. The process of claim 1, wherein the solid BNNT material comprises at least one of a BNNT puff ball, a BNNT powder, a BNNT buckypaper, a BNNT woven fiber mat, and a BNNT porous scaffolding.

3. The process of claim 1, wherein the chamber comprises a Knudsen cell configured to control the evaporation of the first monomer and the second monomer through temperature and pressure regulation within the chamber.

4. The process of claim 1, wherein the first monomer and the second monomer comprise monomers of polyimide.

5. The process claim 4, wherein the first monomer comprises an anhydride, and the second monomer comprises a diamine.

6. The process of claim 1, wherein the first monomer and the second monomer are selected to form a polyamic acid film on the BNNT material.

7. The process of claim 1, wherein the first monomer comprises diamine, and the second monomer comprises anhydride gas, and the first and second monomers are one of introduced into the chamber simultaneously, or introduced alternatingly into the chamber.

8. The process of claim 1, wherein the process continues for about one hour, the first and second monomers are introduced alternatingly into the chamber, and an alternating cycle between the first and second monomers is less than about 100 Hertz.

9. The process of claim 6, further comprising imidizing the functionalized BNNT material to form a polyimide coated BNNT nano-composited material.

10. The process of claim 9, wherein the functionalized BNNT material is imidized.

11. The process of claim 1, wherein the first and second monomers comprise monomers of poly(p-xylene).

12. The process of claim 1 wherein the deposition chamber is connected to a vaporization and pyrolyzing chamber to produce p-xylene monomer from di-p-xylene.

13. The process of claim 12, wherein the feed rate of p-xylene is controlled by the vaporization rate of di-p-xylene.

14. The process of claim 11, wherein the poly-p-xylene coated BNNTs function as surface modified nanotubes.

15. The process of claim 9, wherein the polyamic acid and polyimide coated BNNTs function as surface modified nanotubes.

16. The process of claim 1, wherein the functionalized BNNT material is compressed to form a non-woven mat.

17. The process of claim 1, further comprising suspending the functionalized BNNT material in a non-solvent.

18. The process of claim 17, wherein the non-solvent solution comprises at least one of a metal, a ceramic, and a polymer matrix material.

19. The process of claim 11, further comprising at least one of vacuum filtering the functionalized BNNT material and casting the functionalized BNNT material to form a porous non-woven mats.

20. The process of claim 1, further comprising absorbing a nanoparticle within the functionalized BNNT material.

21. The process of claim 20, wherein the nanoparticle comprises one or more of a medicine, a metal, a ceramic, and a semiconducting material.

22. The process of claim 20, wherein the nanoparticle can be activated by electromagnetic radiation, including photons, or by nuclear radiation.

23. The process of claim 1, further comprising cooling the support to establish a temperature gradient across the solid BNNT material, thereby controlling the condensation of the first monomer and the second monomer onto surfaces of the BNNTs in the solid BNNT material.

* * * * *